(12) United States Patent
Ahn et al.

(10) Patent No.: US 12,186,208 B2
(45) Date of Patent: Jan. 7, 2025

(54) CONTROL OF ELECTRICALLY DRIVEN CORROSION OF MEDICAL IMPLANTS

(71) Applicants: Jeongmin Ahn, Manlius, NY (US); Thomas Welles, Syracuse, NY (US)

(72) Inventors: Jeongmin Ahn, Manlius, NY (US); Thomas Welles, Syracuse, NY (US)

(73) Assignee: SYRACUSE UNIVERSITY, Syracuse, NY (US)

( * ) Notice: Subject to any disclaimer, the term of this patent is extended or adjusted under 35 U.S.C. 154(b) by 209 days.

(21) Appl. No.: 17/738,068

(22) Filed: May 6, 2022

(65) Prior Publication Data

US 2022/0354667 A1 Nov. 10, 2022

Related U.S. Application Data

(60) Provisional application No. 63/184,978, filed on May 6, 2021.

(51) Int. Cl.
  *A61F 2/46* (2006.01)
  *A61F 2/32* (2006.01)
  *G01R 23/00* (2006.01)

(52) U.S. Cl.
  CPC .............. *A61F 2/468* (2013.01); *G01R 23/00* (2013.01); *A61F 2/32* (2013.01)

(58) Field of Classification Search
  None
  See application file for complete search history.

(56) References Cited

U.S. PATENT DOCUMENTS

2016/0015320 A1* 1/2016 Gilbert ................. A61B 5/4851
   600/547
2020/0046224 A1* 2/2020 Jasanoff .............. H01L 31/1136

\* cited by examiner

*Primary Examiner* — Farhana A Hoque
(74) *Attorney, Agent, or Firm* — David L. Nocilly; Bond, Schoeneck & King PLLC

(57) ABSTRACT

A dampening device that can be coupled to a medical implant to eliminate harmful electrical oscillations. The device includes circuity that detects harmful electrical oscillations in the implant. The device also includes circuity that generates cancelling electrical signals that counter the detected electrical oscillations. Alternatively, in a medical implant having a taper junction such as a standard hip implant, resistance welding of the taper junction just prior to surgical implanting may be performed after the appropriately dimensioned components are selected to eliminate a metal on metal interface where corrosion is most likely to occur.

15 Claims, 12 Drawing Sheets

CONTROL OF ELECTRICALLY DRIVEN CORROSION OF MEDICAL IMPLANTS

CROSS-REFERENCE TO RELATED APPLICATIONS

The present invention claims priority to U.S. Provisional App. No. 63/184,978 filed on May 6, 2021.

BACKGROUND OF THE INVENTION

1. Field of the Invention

The present invention relates to medical implants and, more specifically, to techniques for reducing electrically driven corrosion of implanted medical devices.

2. Description of the Related Art

Total hip arthroplasty (THA) is considered to be the most successful orthopedic operation in restoring mobility and relieving pain. In the United States alone, there are over 370,000 THAs performed annually and the number continues to grow each year. It is predicted that over 3 million individuals are currently living with a hip implant. Modular and other metal-on-metal (MoM) implants developed over the past decade can suffer from severe inflammatory reactions of the surrounding tissue caused by the premature corrosion and degradation of the implant.

The new generation of Metal-on-Metal (MoM) implants, commonly Cobalt-Chromium-Molybdenum (CoCrMo alloy ASTM F1357/F75), developed in the past decade, were designed in order to prevent hip dislocation and polyethylene wear complications. It is reported that more than 1 million MoM hip implants have been implanted worldwide. This generation of hip implants, however, suffer from the occurrence of severe inflammatory reactions of the periprosthetic soft tissues. Increased reaction can lead to increased risk of corrosion and wear, resulting in extensive tissue necrosis, injury to abductor muscles and tendons, aseptic loosening/osteolysis, increased revision complications, and significant patient morbidity. As the implant wears and corrodes, metal ions are able to leach into the bloodstream, resulting in heavy metal toxicity, cognitive dysfunction, mitochondrial stress, organ damage, inflammation, cancer, etc.

As a result, implant corrosion and wear-related complications remain a daily concern for implant longevity and patient health. A substantial amount of research has been dedicated to the investigation of mechanically driven fretting and crevice corrosion as the primary mechanism of implant failure. However, the exact mechanism by which hip implant breakdown occurs remains unknown, as current in vitro fretting and crevice corrosion studies have failed to completely replicate the corrosion characteristics of recovered implants. For example, fretting and crevice corrosion are the most common current explanations for implant failure, but these mechanisms focus on a mechanically driven wear while minimizing the potential for a galvanic electrochemical reaction. Additionally, when lab results from simulated fretting corrosion are compared to a failed prosthetic implant, it becomes clear that although fretting may be occurring, it is not a complete explanation. Accordingly, there is a need in the art for an approach that can adequately prevent electrochemical corrosion by addressing the underlying causes.

BRIEF SUMMARY OF THE INVENTION

The present invention is founded on the discovery that when a small electrical oscillation is applied to the CoCrMo alloy used in medical implant devices, the resulting corrosion begins to replicate that which is seen in recovered prostheses. As similar oscillations can be experienced by the implant in response to common electromagnetic radiation sources, the present invention provides approaches for mitigating or eliminating the electrical oscillations and thus preventing a cause of corrosion and device failure.

In a first embodiment, the present invention comprises a dampening device coupled to the implant and including circuity that detects harmful electrical oscillations in the implant as well as circuity that generates cancelling electrical signals that counter the detected electrical oscillations.

In a second embodiment, the present invention comprises resistance welding of the taper junction in an implant to eliminate the metal on metal interface that provides a primary corrosion location.

BRIEF DESCRIPTION OF THE SEVERAL VIEWS OF THE DRAWING(S)

The present invention will be more fully understood and appreciated by reading the following Detailed Description in conjunction with the accompanying drawings, in which.

Figure 4:
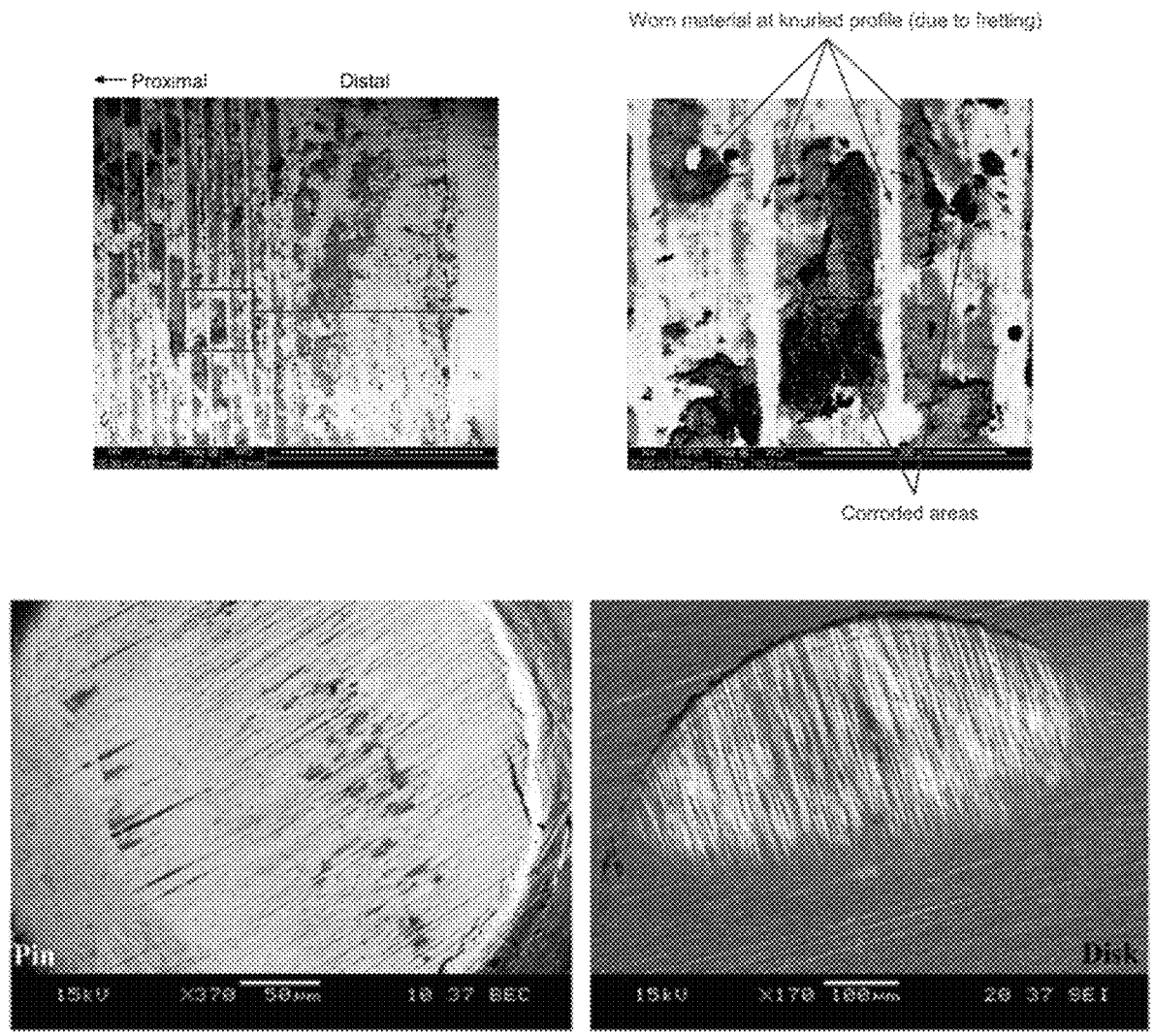

FIG. 4 is a series of images showing: (A) surface damage to the CoCrMo neck, mainly in the distal medial area and scanning electron microscope (SEM) image with a higher magnification showing both mechanical fretting wear and corrosion damage on removed implant, and (B) backscatter and secondary electron mode SEM micrographs of pin and disk surfaces of CoCrMo obtained at the end of fretting corrosion in lab testing.

Figure 5:
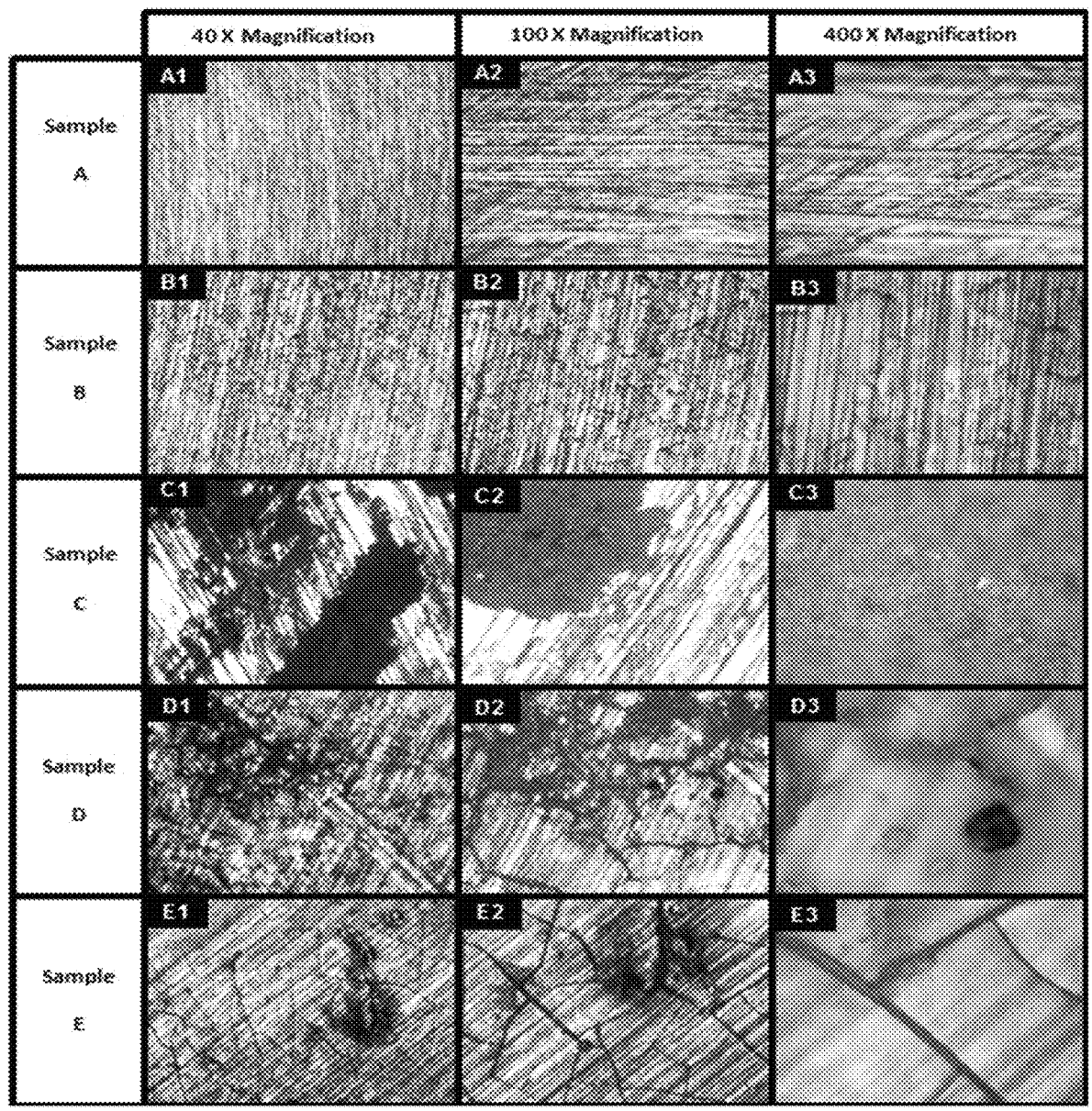

FIG. 5 is a series of images of optical microscopy micrographs of 5 samples under varying electrical test signals, where Sample A is a baseline ASTM F75 CoCrMo alloy, Sample B is an ASTM F75 CoCrMo alloy placed in simulated synovial fluid (50/50 DI water/FBS) with no electrical signal, Sample C is an ASTM F75 CoCrMo alloy in simulated synovial fluid with Vrms=0.67 V pulsed DC electrical signal, Sample D is an ASTM F75 CoCrMo alloy in simulated synovial fluid with 100 MHz Sine wave at 250 mV peak-to-peak amplitude AC electrical signal, and Sample E is an ASTM F75 CoCrMo alloy in simulated synovial fluid with 250 mV peak-to-peak amplitude random noise AC electrical signal.

Figure 6:
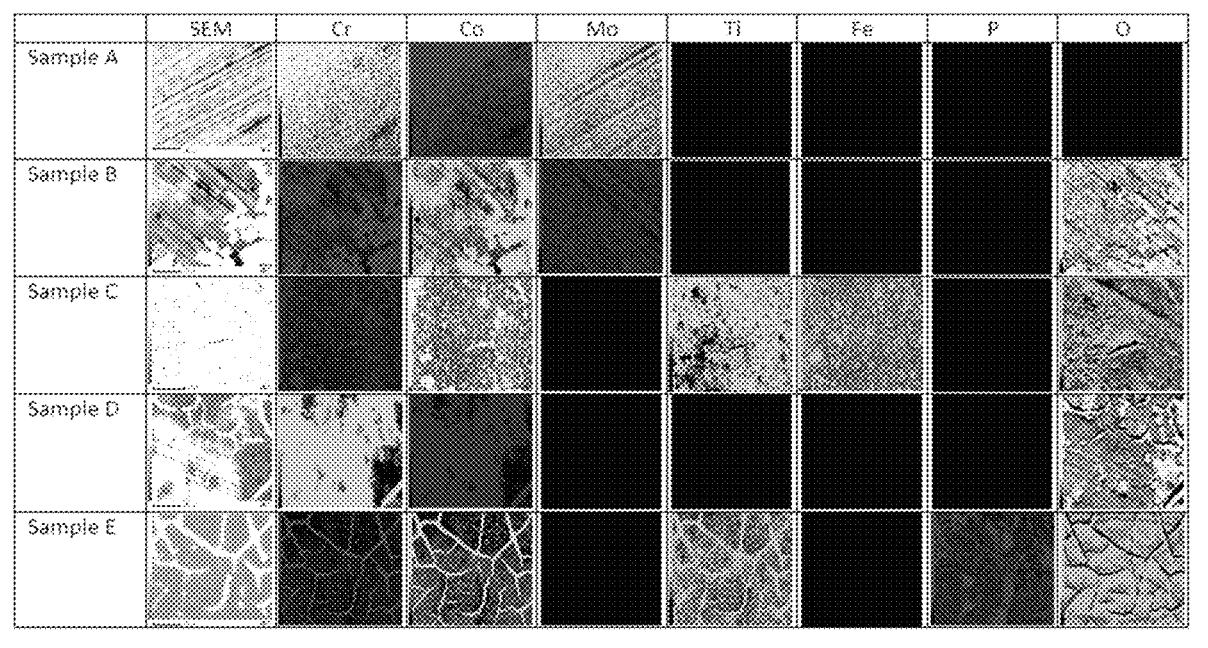

FIG. 6 is a series of micrographs of SEM EDS element mapping of 5 samples under varying electrical test signals, where Columns A1-E1 are SEM micrographs of 5 samples selected for elemental mapping after 10 days, Columns 2-8 show detected elements on the sample surface (Chromium-Cr, Cobalt-Co, Molybdenum-Mo, Titanium-Ti, Iron-Fe, Phosphorous-P, and Oxygen-O, Rows A-E identify the sample tested (Samples A through E as described above).

Figure 7:
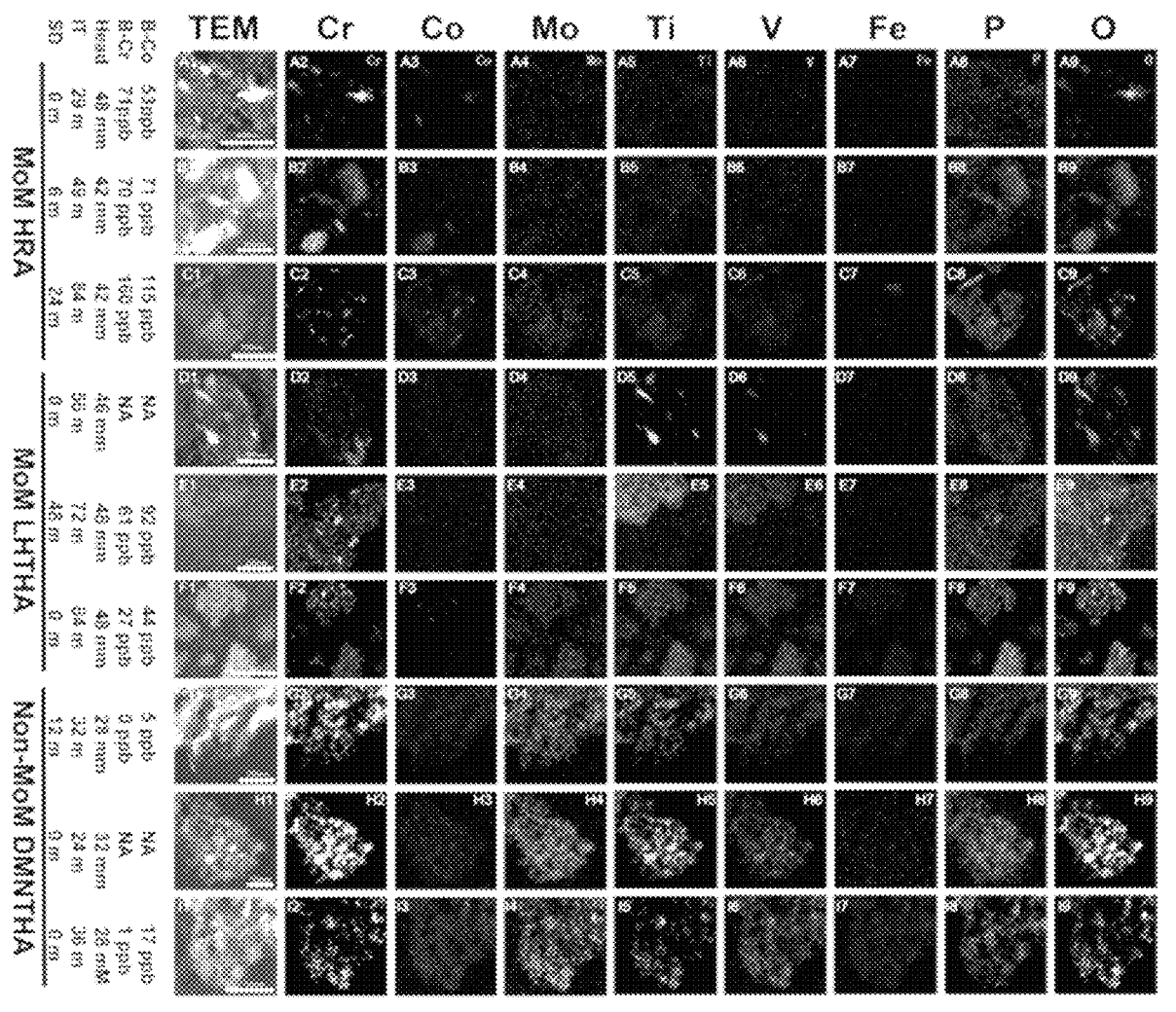

FIG. 7 is a series of micrographs of TEM EDS element mapping of three samples of each class of hip arthroplasty.

Figure 8:
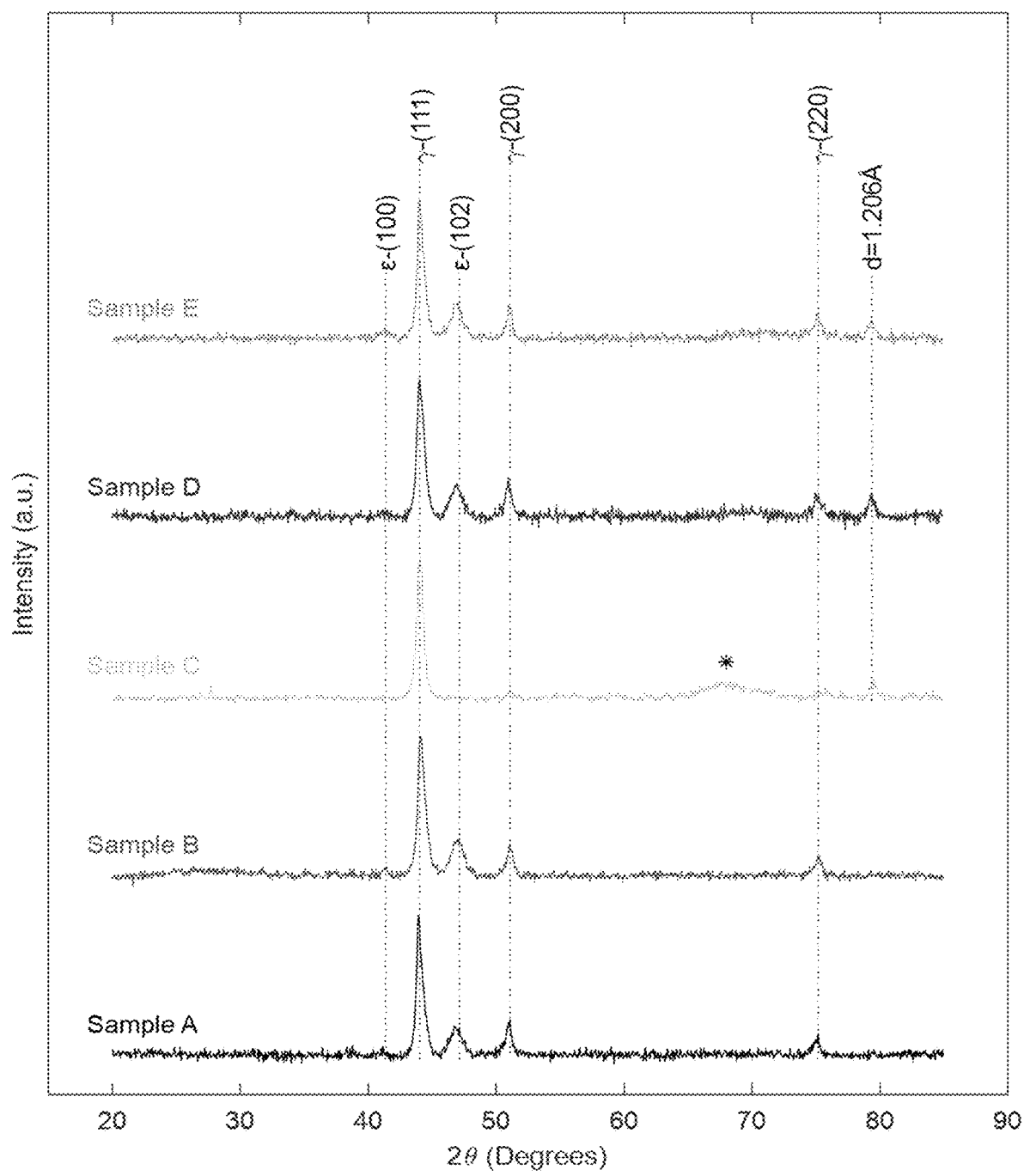

FIG. 8 is a series of XRD patterns of base alloy and corrosion samples tested (Samples A through E as described above).

Figure 9:
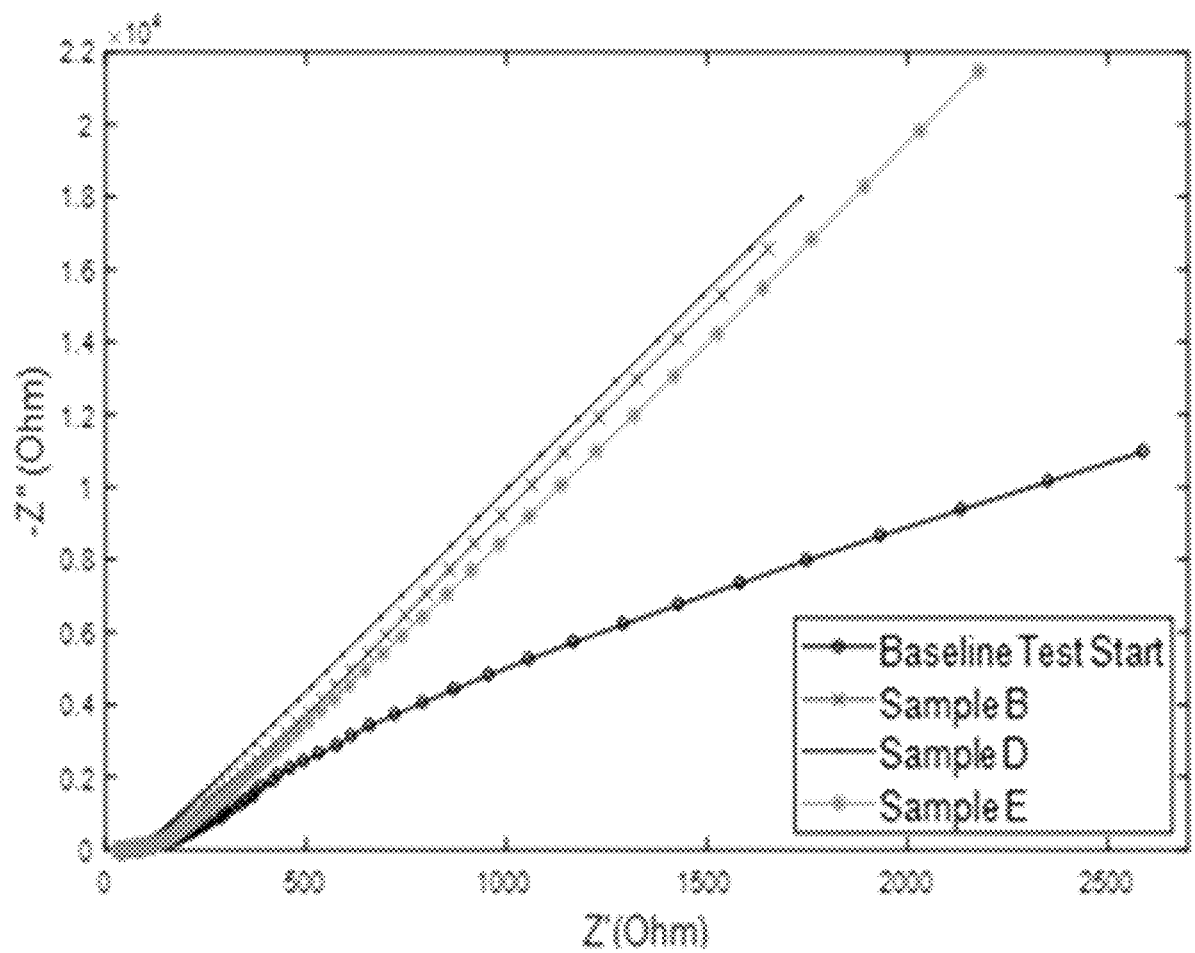

FIG. 9 is a first micrograph of EIS analysis after 10 days of testing within the simulated synovial fluid test bed compared to the baseline scan on the first day of testing (Samples A through E as described above).

Figure 10:
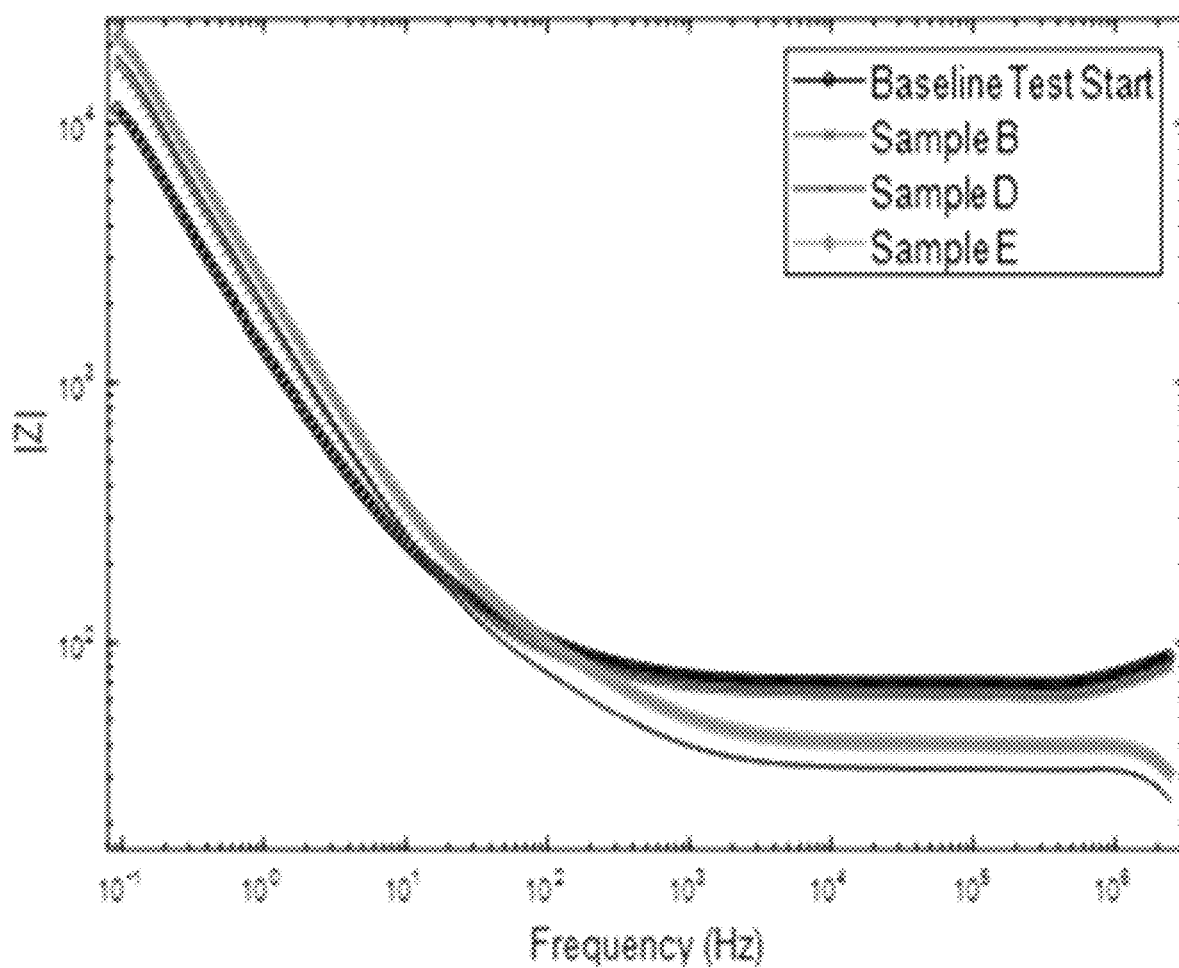

FIG. 10 is a second micrograph of EIS analysis after 10 days of testing within the simulated synovial fluid test bed compared to the baseline scan on the first day of testing (Samples A through E as described above).

Figure 11:
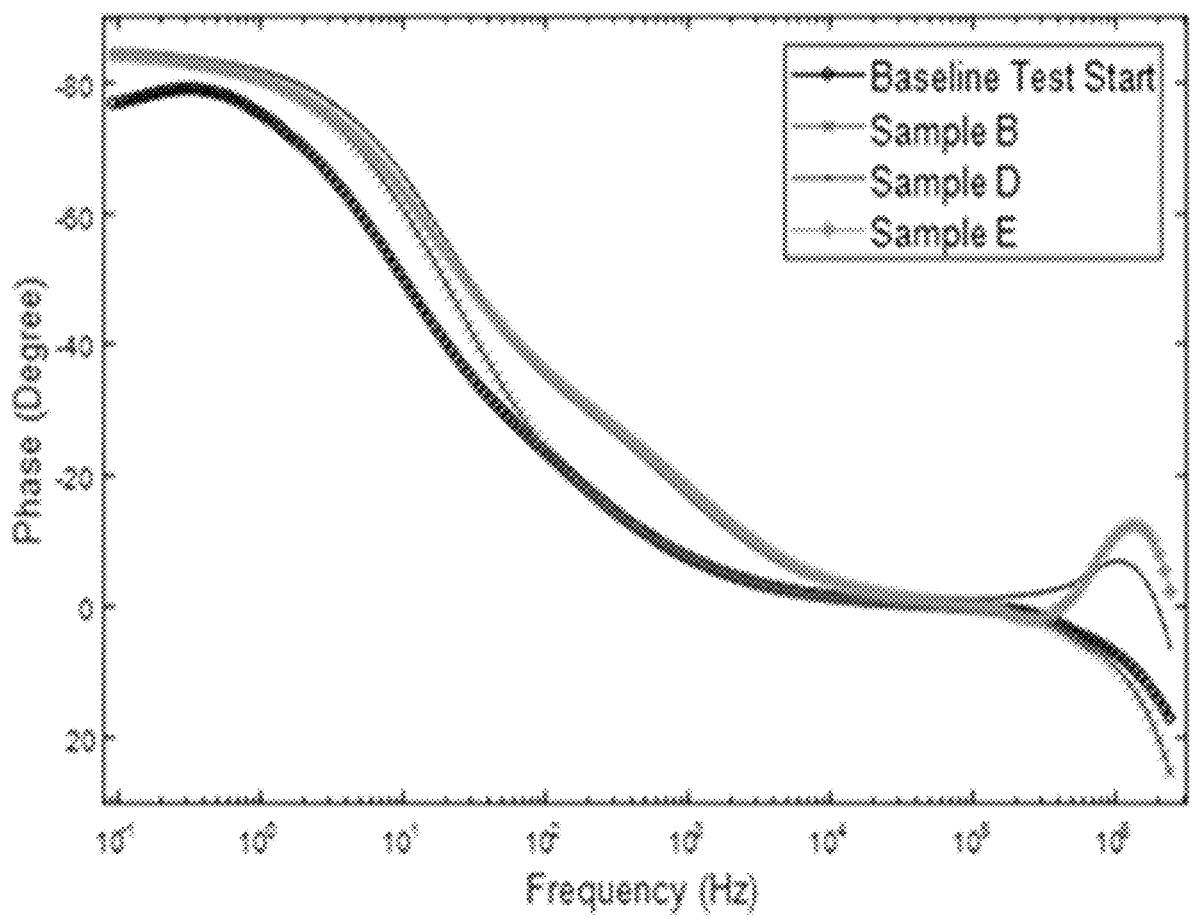

FIG. 11 is a third micrograph of EIS analysis after 10 days of testing within the simulated synovial fluid test bed compared to the baseline scan on the first day of testing (Samples A through E as described above).

Figure 12:
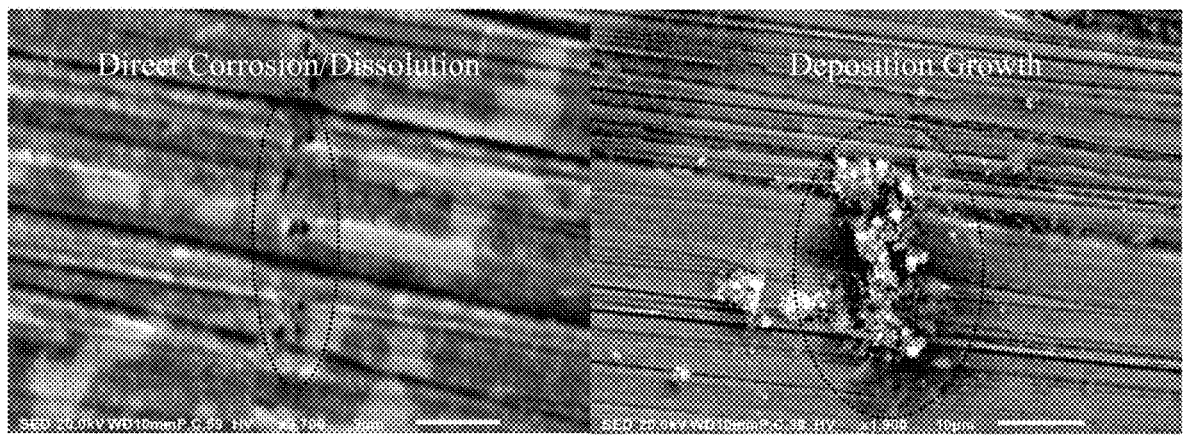

FIG. 12 is a pair of images providing a comparison of surface modification types on Sample E under high magnification SEM imaging, where the left image shows direct corrosion/dissolution and the right image shows deposition growth.

DETAILED DESCRIPTION OF THE INVENTION

Figure 1:
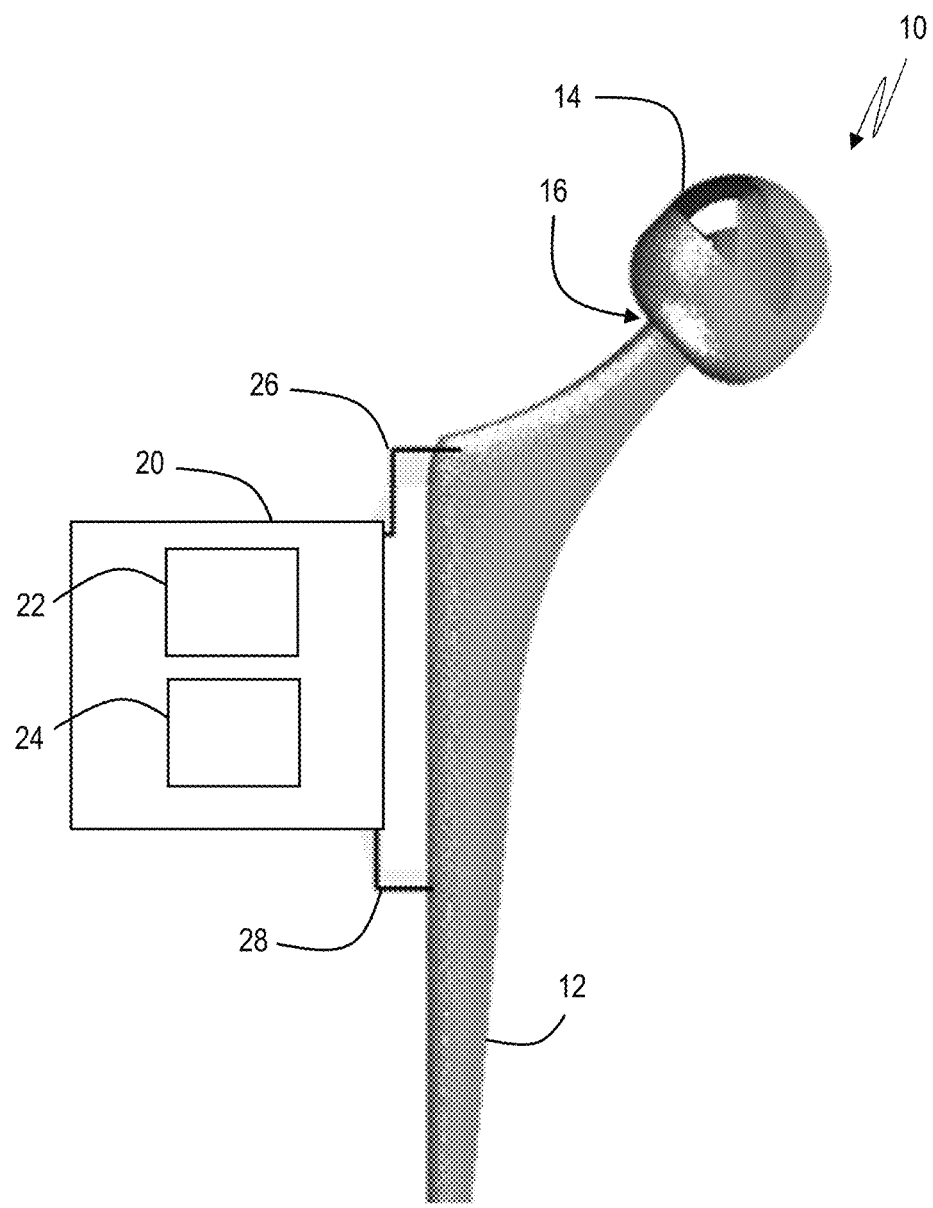
FIG. 1 is a schematic of an embodiment of a device for cancelling electrical oscillation in a medical implant according to the present invention.
Figure 2:
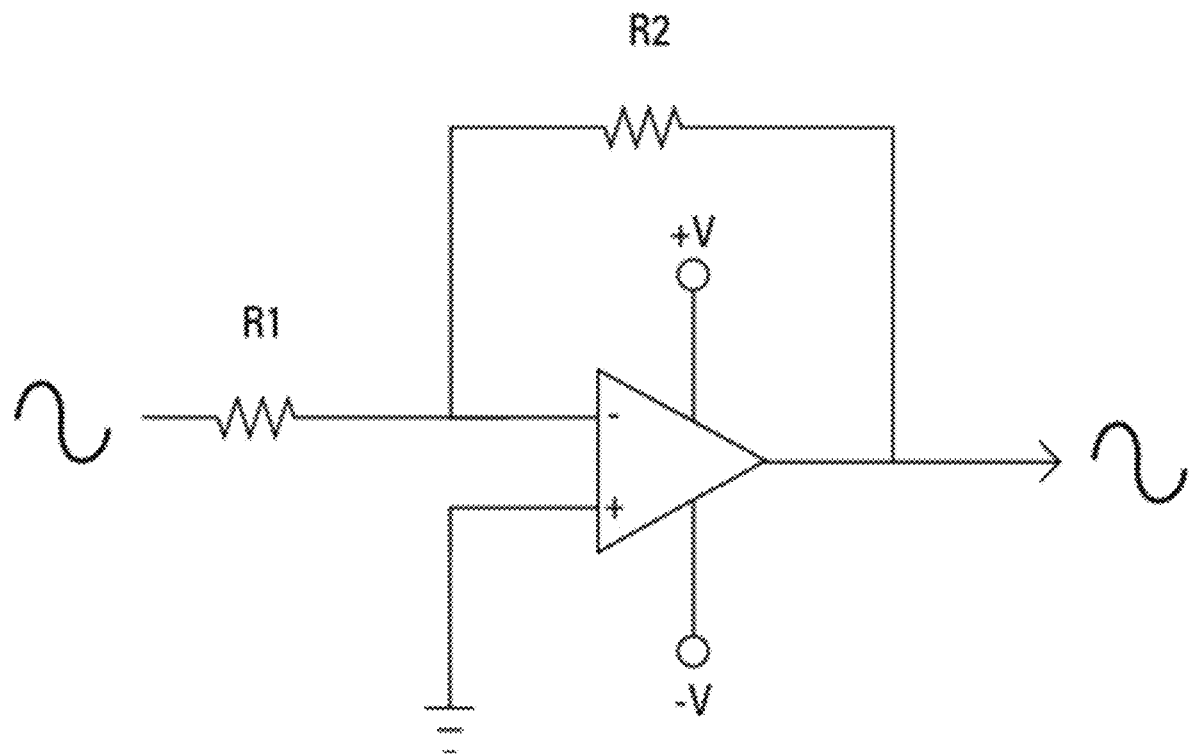
FIG. 2 is a schematic of a noise cancelling circuit acceptable for the present invention.

Referring to the drawings wherein like reference refer to like parts throughout, there is seen in FIG. 1 a schematic of a hip implant 10 that can be subject to electrical oscillations in response to electromagnetic radiation sources that are regularly encountered by the patient having implant 10 and develop corrosion as a result. Implant 10 generally comprises a femoral stem 12 that is secured to a femoral head 14. Typically, stem 12 and head 14 are coupled together at the time of surgery via a taper junction 16 so that a particularly sized stem 12 and particularly sized head 14 can be selected for the best fit in a specific patient. Minor electric potential oscillations in hip implant 10, of similar frequency and magnitude to those that can result from exposure to ambient electromagnetic waves, can interact with the metal of implant 10 and cause electrochemical reactions within the synovial fluid environment that lead to corrosion. For example, in lab experiments, titanium, phosphorous, and oxygen deposition onto the surface of ASTM F75 CoCrMo metal alloy test specimens that resulted from electric potential oscillations stemming from electromagnetic radiation matched the chemical composition of previously retrieved wear particles from failed patient prosthetics. These results demonstrate that the electric potential oscillations and ensuing electrochemical activity excites two corrosion failure modes: direct dissolution of the medically implantable alloy, leaching metal ions into the body, and surface deposition growth, forming the precursor of secondary wear particles.

The present invention provides approaches for the reduction or elimination of electrical activity on the implant, thereby preventing electrochemical corrosion. As seen in FIG. 1, in a first embodiment, the present invention comprises an active electrical activity dampening device 20 coupled to implant. Dampening device 20 includes a first set of circuitry 22 configured to detect and identify electric potential oscillations in implant 10, such as those that result from exposure to ambient electromagnetic waves. Dampening device 20 includes a second set of circuitry 24 configured to apply a cancelling electrical signal, such as a signal that is 180 degrees of out phase with the electric potential oscillations in implant 10 as detected by first set of circuitry 22. Dampening device 20 may include two or more probes 26 and 28 electrically coupled to implant 10 and spaced apart from each other to sense and then cancel any electrical activity in the implant. Dampening device 20 may be positioned internally or externally of implant 10 and acts as an active electrical activity damper.

Dampening device 20 may leverage the technologies used by active noise cancelling systems. Dampening device 20 and associated circuitry may be analog or digital. Dampening device 20 may be constructed to dampen the electrical activity induced by manmade sources of electromagnetic radiation. Namely, dampening device 20 will dampen oscillations ranging from 60 Hz to the GHz range. Focus may be placed on dampening in the 60 Hz-1 kHz and the MHz-GHz ranges. This is designed to eliminate common oscillations resulting from building power (~60 Hz) and the dense communication bands, respectively.

Figure 3:
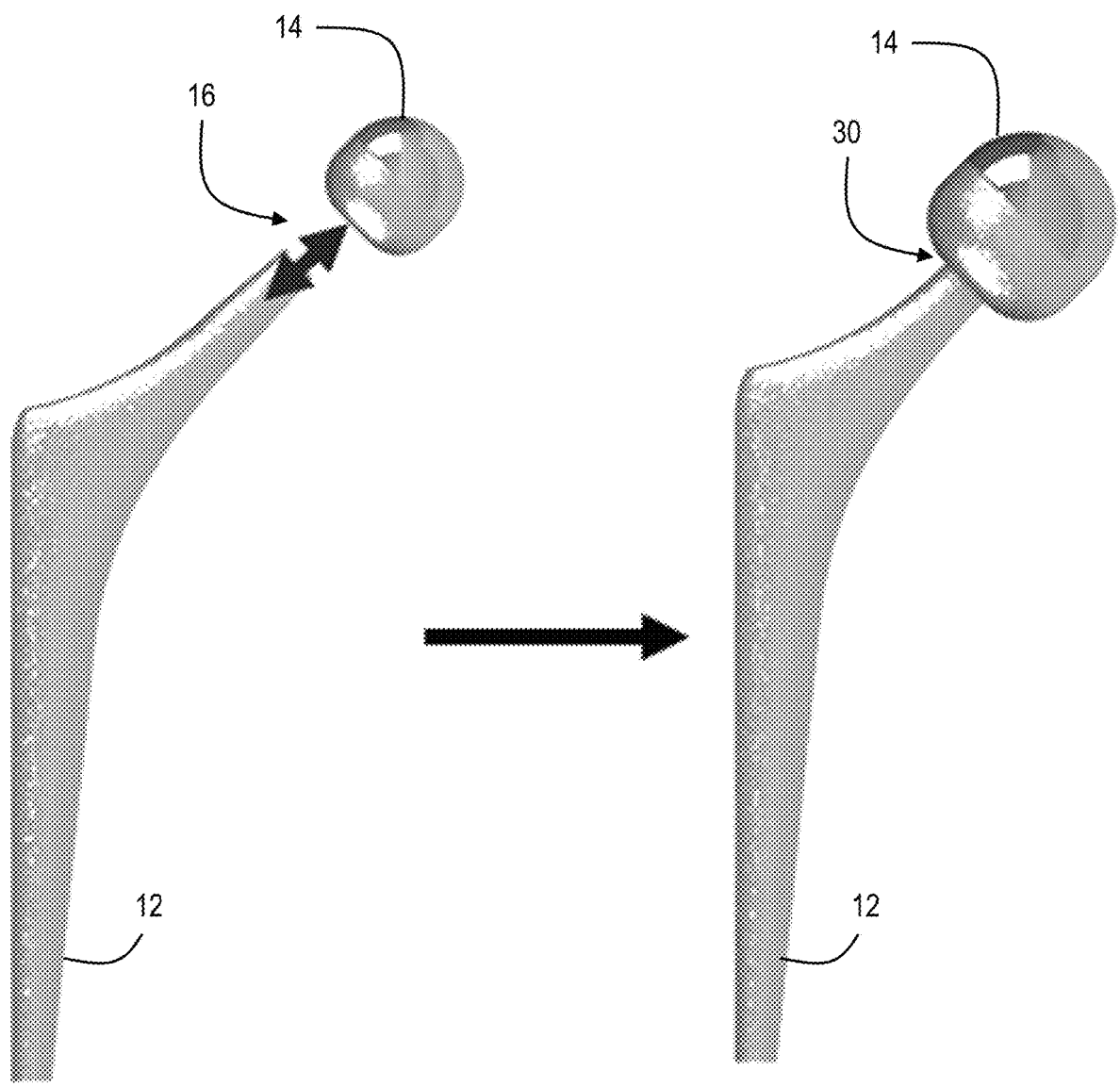
FIG. 3 is a schematic of a fused taper function according to the present invention to reduce electrical oscillation in a medical implant according to the present invention.

In an analog configuration the dampening device will utilize simple circuitry, such as an operational amplifier in a unity inverting configuration. Referring to FIG. 3, the exemplary configuration, the resistive magnitude of R1 and R2 may be selected in accordance to the incoming signal, but R1 must equal R2, to act as a unity operational amplifier. In FIG. 3, the input refers to the incoming electric signal from the implant and the output refers to the modified signal used for dampening by deconstructive interference. Additionally, a bipolar junction transistor in a common phase splitting circuit, or a metal oxide semiconductor field effect transistor in a similar circuit, may be used to produce an inverted or 180° phase shifted signal. One or more of the suggested analog circuits may be used in combination to achieve the desired results. In all configurations the ground reference for the circuitry, input signal, and output signal must be the same reference. The input signal probe and the output signal probe should not be one and the same.

In a digital configuration, a common microcontroller with an embedded analog to digital converter, and arbitrary waveform generator may be used. In such a configuration, as similar to the analog circuity, the microcontroller may record the input signal from the implant. The signal may then be converted to a digital signal, phase shifted 180°, and sourced as an interference output signal. In such a configuration, a constant feedback loop may be added to the controller to determine of the supplied signal is achieving the desired results. The feedback loop may then alter the phase shift, time delay, or amplification of output signal to achieve the desired result.

In all configurations, the circuitry may require a separate power source. This may be achieved by a long duration battery, implanted or external to the patient. The battery source should be designed to be easily changed, either surgically or externally. Additionally, a modern kinetic charging device may be incorporated into the circuitry, so that patient natural movements will recharge an implanted battery.

Referring to FIG. 3, in another embodiment, the present invention involves the reduction of metal-on-metal (MoM) interfaces in implants 10. Each MoM interface allows for the penetration of synovial fluid, creating a metal-synovial fluid-metal interface. Each metal interface generates additional electrical charging under ambient electromagnetic radiation. As a result, this embodiment of the present invention seeks to reduce the number of MoM interfaces without compromising the modularity of current prosthesis system. For example, the primary junction where corrosion occurs in a hip implant is in the taper junction used to couple femoral stem 12 and femoral head 14. During a typical surgery, a surgeon selects the appropriately sized femoral stem 12 and femoral head 14 for the patient and then joins the femoral stem 12 and femoral head 14 together using the taper junction and then implants the femoral stem 12 and femoral head 14. The present invention mitigates the potential for corrosion of this metal-on-metal (MoM) interface by using resistance welding to join the metals of the femoral head and neck. After selecting the appropriately dimensioned femoral stem 12 and femoral head 14 for the patient, femoral stem 12 and femoral head 14 are coupled together in the conventional manner and then positioned within a resistance welding machine. Femoral stem 12 and femoral head 14 are then subjected to resistance welding until the taper junction becomes a continuous metal junction 30, thereby preventing the penetration of synovial fluid into the taper junction once implant 10 is positioned in the patient.

Example

Samples were cut from medical grade ASTM F75 round stock to serve as a simulated hip implant. The chemical composition of the alloy is found below in Table 1.

TABLE 1

Elemental analysis of CoCrMo metal alloy used in testing provided by United Performance Metals. Testing completed by Carpenter Technology Corporation
ASTM F75 CoCrMo Alloy Chemical Composition by Weight Percent

| Elements | Weight % |
|---|---|
| Cobalt | 65.05 |
| Chromium | 27.76 |
| Molybdenum | 5.54 |
| Trace Elements | |
| Carbon | 0.05 |
| Manganese | 0.79 |
| Silicon | 0.59 |
| Phosphorous | 0.003 |
| Sulfur | 0.005 |
| Nickel | 0.04 |
| Copper | 0.01 |
| Aluminum | 0.04 |
| Nitrogen | 0.175 |
| Titanium | 0.004 |
| Tungsten | 0.02 |
| Boron | 0.001 |
| Iron | 0.12 |

The 1 inch diameter round stock was cross cut, resulting in a ⅛ inch thick disc. The disc was further sectioned into quadrants. Each quadrant received a 3/32 inch hole for future wire attachment. The samples were polished to remove any surface imperfections with a Buehler Metasery 250 Grinder/Polisher and P400 grit silicon carbide wet polishing paper. The curved face of the sample was further polished with P2500 grit silicon carbide wet polishing paper to develop a high sheen, mimicking that of the bearing surface of a hip prosthetic.

Each sample was then wired with a medical grade one titanium wire lead, representative of titanium hardware used in the installation of prosthetic hips. The chemical composition of the titanium wire used is shown in Table 2 below.

TABLE 2

Elemental analysis of Titanium Grade 1 wire used in testing provided by TEMCo Industrial
ASTM F76 Ti Grade 1 Chemical Composition by Weight Percent

| Elements | Weight % |
|---|---|
| Titanium | ≥99.6 |
| Trace Elements | Maximum Weight % |
| Nitrogen | 0.03 |
| Carbon | 0.08 |
| Hydrogen | 0.01 |
| Iron | 0.20 |
| Oxygen | 0.18 |
| Maximum Total Residuals | 0.40 |

Two of the prepared samples were placed into each Pyrex petri dish, and subsequently submerged in 100 mL of simulated synovial fluid. Each wire lead exited the side of the petri dish under the lid. The simulated synovial fluid was created following the industry standard of a 1:1 (by volume) mixture of fetal bovine serum (FBS), purchased from Millipore Sigma, and de-ionized (DI) water. The exact chemical composition of the FBS is unknown, but it is known to contain a complex mixture of salts, proteins, and lipids. Any element identified during testing not reported in the metal samples or in the preparation of samples, is assumed to be a result of the FBS.

The samples subjected to electrical activity were connected to a frequency generator for simulated electrical oscillation. A bacteria culture was taken of the simulated synovial fluid and placed within the incubation oven alongside the test specimens in order to identify any contamination within the test fluid. The test specimens were then placed into a faraday cage within an incubation oven at 37° C. for 10 days. For each test, two samples were subjected to electrical oscillations and one baseline sample was shielded from electrical oscillation. Each test run was repeated, resulting in four samples for each test condition to ensure repeatability, as well as two baseline samples. During the duration of the lab testing, the samples subjected to true AC oscillations were connected to an electrochemical impedance spectroscopy (EIS) machine. An EIS response frequency sweep was performed on each specimen daily from $1.5 \times 10^6$ Hz to $5.0 \times 10^{-2}$ Hz, in order to characterize the electrochemical properties of each specimen. At the conclusion of each test, the samples were removed from the testing solution and rinsed with DI water. The samples were then gently wiped clean with Kimwipes™ to remove any loose material. Following this, the samples were rinsed again with DI water, dried, and bagged for analysis.

Five test conditions were studied to represent a viability study for the first attempt to utilize an oscillatory electrochemical reaction phenomenon to replicate the chemical corrosion of implanted ASTM F75. Samples from test condition A serve as the metal baseline. These samples were not subjected to any testing after sample preparation. Therefore, Sample A represents the clean ASTM F75 sample. Samples from test condition B were placed into simulated synovial fluid with no electrical activity. Samples from test condition C were subjected to a pulsed direct current (DC) signal, consisting of a pulse width modulated signal at a 5% duty cycle (900 μs pulse on a 20,000 μs period), resulting in a root mean square voltage of 0.67 V. This test condition is meant to investigate an electrophoretic deposition type corrosion mechanism. Skin electrode testing, as well as previously reported literature, has indicated a potential DC offset of skin electrical activity in the range of 500~800 mV. Samples from test condition D were subject to a clean sine wave oscillation at 100 MHz and a peak to peak voltage magnitude of 250 mV. The voltage magnitude was selected in accordance to previously published literature for recorded interference in nerve conduction studies, skin electrode data, and experimental work on biological effects of external electric fields. The corrosion mechanism was additionally assumed to be a high frequency phenomenon, and as such, the frequency of oscillation was set to the generator's upper resolution limit. Samples from test condition E were subjected to a random noise oscillation at a peak to peak amplitude of 250 mV with embedded frequencies up to 100 MHz and no DC offset. This is meant to investigate the effect of noise in comparison to the Sample D test condition.

Samples from test conditions A, B, C, D, and E will be referred to simply as Sample A, etc. and all results shown will be indicative of all samples from that test condition.

When electrical activity was placed on the samples within the simulated synovial fluid, samples C-E began clear corrosion activity. No sample tested here underwent mechanical wear, yet contrary to many theories, corrosion began. The type of surface reaction appears to have a dependency on the frequency of electrical oscillation, indicated by the difference in the appearance of the surface after testing between samples C, D, and E. The combination of samples C-E appear to recreate the corroded areas highlighted by Oskouei et al. in FIG. 4A. An application of oscillatory electrical activity, in a magnitude similar to that experienced in daily life, begins to replicate the tribocorrosive behavior seen in failed orthopedic implants.

The surface composition of each sample was then analyzed by energy dispersive X-ray spectroscopy (EDS), the results of which were subsequently compared to published data on the analysis of wear particles retrieved from patient tissue.

The samples with electrical activity (Rows C-E) show significant surface modification when compared to the samples without electrical activity (Row B) of FIG. 6. The surface modification consist primarily of Titanium, Iron, Phosphorous, and Oxygen.

The elemental composition differed for each type of electrical oscillation. Sample C was subjected to a pulsed DC signal to identify any effects of DC offset as well as the potential of electrophoretic deposition (EPD). The surface analysis shows removal of Mo and addition of Ti, Fe, and O. The Mo is assumed to have entered solution or is masked by surface deposition. Fe and O are assumed to have deposited from the FBS, whereas the Ti is assumed to have migrated from the wire lead. This surface change is not directly attributed to the potential of EPD because all samples under this test condition showed similar chemical changes. Typically, in EPD, it is expected that charged particles held in colloidal suspension move toward and deposit on the working electrode and move away from the counter electrode. However, in this instance, both electrodes are composed of identical materials and display similar chemical change. It is possible that EPD contributed to the transfer of Ti from the wire lead to the sample surface, yet Sample E also illustrates migration of Ti without the potential for EPD. Therefore, further testing is required to investigate the potential for EPD.

Sample D, under the influence of a clean sine wave oscillation, shows oxygenation of the surface from the FBS, and similar to Sample C, shows loss of Mo.

Sample E, subjected to random noise, shows significant phosphorus presence, unlike any other sample. The phosphorous is assumed to be precipitating onto the surface from the FBS. Although, the ASTM F75 stock used is reported to have 0.003 percent by weight, as shown in Table 1, concentration of phosphorous, all samples were cut from the same stock and no other sample shows significant phosphorous concentration under EDS analysis. Moreover, all samples tested under condition E showed significant presence of phosphorous, whereas all other test condition samples did not show the presence of phosphorous. Sample E, additionally, showed oxygenation of the surface, Ti transfer from the wire lead, and decreased Mo at the surface.

The combination of chemical compositions from the above test conditions begin to replicate that of wear particles reported previously in literature. It is therefore imperative to systematically compare these novel results with previous studies on failed hip implants.

FIG. 7 is taken for comparison from a previous study in which the surrounding tissue of a failed hip implant was sampled to identify wear particles that had released from the surface of the implant. The retrieved particles were analyzed for elemental composition. In FIG. 7, Column A1-I1 are TEM micrographs of 9 samples selected for element mapping and all samples contain variable amounts of Cr particles (A2-I2), P (A8-I8) and O (A9-I9). A small number of high electron density particles in the MoM hip resurfacing arthroplasty (HRA) (A3-C3) and the MoM large head total hip arthroplasty (LHTHA) (D3-F3) groups, and the particles in the Non-MoM dual modular neck total hip arthroplasty (DMNTHA) group (G3-I3) contain Co. High concentration of Mo is present in the Non-MoM DMNTHA group (G4-I4) and barely detectable in MoM HRA and MoM LHTHA groups. Ti and V co-exist in the MoM LHTHA (D5-F5, D6-F6) and the Non-MoM DMNTHA (G5-I5, G6-I6) groups but are not detectable in the MoM HRA group (A5-C5, A6-C6). Fe is detected in some samples (C7, H7 and I7) and does not co-localize with other metal particles. P co-exists with O but its concentration is lower than O·B—Cr, blood Cr ion concentration; B—Co, blood Co ion concentration; Head, femoral head size; IT, implant time; SD, symptom duration. Scale bars: B1, D1, E1, G1=200 nm; A1=400 nm; C1, I1=700 nm; F1=1000 nm. As illustrated in FIG. 7, the recovered wear particles consisted primarily of Titanium, Iron, Phosphorous, and Oxygen. An inflammatory particle was identified to potentially be $Cr_2O_3$. This indicates that the generation of wear particles result from a fundamental chemical change of implanted metal.

Current studies of crevice and fretting corrosion do not adequately replicate the significant chemical change seen in implanted devices. The elemental mapping of retrieved wear particles closely matches the results generated by electrical oscillation in FIG. 6, above. The experimental work done here was able to demonstrate a precipitation of Titanium, Iron, Phosphorous, and Oxygen as seen in the retrieved particles. The experimental work, however, did not replicate the precipitation of Vanadium. The chemical composition of the patient's synovial fluid is not known, nor is the inclusion of additional fixtures within the patient, so there is no comparison of Vanadium concentration between the patient and this lab testing.

In order to elicit information pertaining to any crystallographic structure change, each sample was further analyzed via X-ray diffraction (XRD). FIG. 8 illustrates the XRD pattern of each corrosion sample.

Sample A, representing the untested CoCrMo alloy, displays a diffraction pattern with peaks at 2θ equal to 41.3°, 44.1°, 47.1°, 51.0°, and 75.1°. The diffraction pattern is consistent with prior published work, identifying the majority of the material as a face centered cubic (FCC) γ-(Co, Cr, Mo) crystallographic structure indicated by major peaks at 44.1° and 51.0°. Lesser peaks at 41.3° and 47.1° indicate a small amount of hexagonal close pack (HCP), ε-(Co, Cr, Mo).

The XRD diffraction pattern for Sample B, shielded from electrical activity within simulated synovial fluid, shows no change when compared to Sample A. Therefore, it is concluded that no crystallographic structure change occurred to the metal alloy within the simulated synovial fluid over the test duration.

Sample C, subjected to pulsed DC electrical signal, shows significant variation in XRD diffraction pattern when compared to all other samples. Sample C maintains the major peak at 44.1° from the original alloy, but all other peaks from the original alloy are not present. Sample C shows an additional minor peak at 79.3°, labeled with inter-plane spacing d=1.206 Å, and a broad peak between 2θ~65° and 2θ~75°, labeled as *. The lack of the original pattern and creation of a broad, non-descript, peak is believed to be the addition of amorphous material onto the surface of the sample, likely, through EPD and does not indicate structural change within the sample. Previous literature on the analysis of in-vivo corrosion products has shown that the original diffraction pattern persists with the potential for additional new peaks. Therefore, the pulsed DC electrical signal, allowing for EPD, is most likely not the cause of corrosion on implanted CoCrMo.

However, if a pure oscillatory electric field is established on samples within simulated synovial fluid, such as with Samples D and E, a clear modification of the original crystallographic structure without the addition of amorphous surface material is evident. Sample D, subjected to a 100 MHz sine wave, and Sample E, subjected to random AC noise, both show the original diffraction pattern of Sample A, peaks at 2θ equal to 41.3°, 44.1°, 47.1°, 51.0°, and 75.1°, with the addition of a substantial peak at 79.3°, with inter-plane spacing d=1.206 Å. Therefore, the majority of the sample is maintained as FCC γ-(Co, Cr, Mo) with a small amount of HCP ε-(Co, Cr, Mo). The additional peak, in conjunction with EDS data given in FIG. 6, is believed to be a crystalline product containing Cr, O, and/or P.

It is hypothesized that the chemical composition of the deposited particulate for the in vitro testing may be tuned in future work via manipulation of the frequency and magnitude of the electrical oscillation to exactly match that of the recovered particles. Therefore, this newly identified electrochemical corrosion mechanism is expected to initiate what has been considered the tribocorrosive decay seen in implanted devices.

In order to identify, understand, and potentially predict this electrochemical corrosion mechanism more holistically, the electrochemical behavior change over time is investigated.

The electrochemical behavior of specimens B, D, and E is characterized by the EIS frequency sweep test shown above in FIG. 9 through 11. Sample C was not characterized by EIS analysis due to machine limitations in conjunction with the pulsed DC signal. The curve labeled 'Baseline Test Start' indicates the electrochemical behavior of all samples prior to testing when first placed into the simulated synovial fluid. The curve labeled as 'Sample B' is the same as in previous figures and is present to act as a control for the experiment. Sample B is allowed to sit within the test fluid, but is not subjected to any forced electrical oscillations, therefore, any changes seen in Sample B may be thought of as baseline changes. As the Sample B concludes testing, there is a clear increase in the imaginary impedance, or reactance of the specimen, FIG. 9, with a minor increase in overall impedance magnitude, FIG. 10, and phase shift at low frequency (<100 Hz), FIG. 11. This minor shift is not to be unexpected as the simulated synovial fluid ages, and galvanic interaction occurs between the metal and the fluid. However, above 100 Hz there is no significant deviation from the baseline data collected at the start of the test. Reviewing the electrochemical behavior of Samples D and E against Sample B and the test initiation data indicates significant deviation from the control and baseline above ~10 Hz. Samples D and E showed significantly lower magnitude of total impedance at high frequency, FIG. 10. Total impedance magnitude of Sample D was nearly ½ of an order of magnitude smaller than the control sample, indicating significant potential for high frequency electrochemical reactions. Although Sample E closely followed the changes seen in Sample D, but to a lesser extent at high frequencies, the low frequency behavior of Sample E was markedly different from any other trend. Sample E showed the greatest amount of reactance, FIG. 9, at low frequency, potentially indicating the possibility of increased capacitance like behavior. Each signal therefore elicits a separate, complex electrochemical behavior. This is the first documentation of this phenomenon within a simulated hip environment to the knowledge of the author, and requires significant study to develop a complete description and predication of the electrochemical response resulting from varying electrical signals on an implanted metal.

The electrical oscillation induced at the implant's surface, as represented by Sample D and E, incites active electrochemical reactions within the surrounding synovial fluid, generating surface modification through ion exchange and deposition growth. The type of surface modification is classified as direct corrosive/dissolution of the base material and as deposition growth, resulting in the development of wear particles. The distinction is pictorially described in the high magnification SEM images of Sample E given in FIG. 12.

The direct corrosion/dissolution shown on the left of FIG. 12 is categorized by the formation of pits on the metal's surface. This indicates that the metal has begun to directly dissolve into the synovial solution, causing direct degradation to the implant. This is in contrast to the deposition growth surface modification, shown on the right of FIG. 12, in which solids precipitate out of solution and bond to the surface of the metal. The crystalline structure of the surface growth are then scraped from the implant's surface when subjected to mechanical wear during natural patient movement, and the free crystalline structure then becomes imbedded within the surrounding tissue causing inflammation, pain, and leading to potential tissue necrosis. The corrosion then proceeds in a cyclic pattern until the implant must be revised or removed and replaced.

Additionally, the EIS characterization indicates the potential for increased electrochemical activity as the metal ages within the implanted environment. The decrease in the total magnitude of impedance at high frequency indicates the potential for a self-accelerating corrosive mode. It is therefore expected that this phenomenon may cause the unexpected rapid corrosion of hip implants after years of seemingly stable operation within the patient.

This discovery rejects the traditional approach to metal corrosion within human subjects. Electrochemical surface reactions are active prior to mechanical wear mechanisms, indicating that the electrochemical activity on the implant is a primary cause of breakdown and not a secondary or tertiary result of prior wear. Therefore, this electrochemical corrosion works in cooperation with fretting/crevice type corrosion for the complete breakdown of the implanted hip.

The exact electrical signal capable of replicating the complete chemical corrosion of implanted CoCrMo hip prosthetics must continue to be actively investigated. The work described here represents a viability study into the potential for natural electrical oscillations, developing on the prosthetic, to act as an incipient mechanism of corrosion. Significant further study is required to fully understand this phenomenon and its interdependencies on previously investigated fretting/crevice corrosion.

Although CoCrMo ASTM F75 corrosion has been the focus of corrosion within the orthopedic industry, this phenomenon is expected to potentially be present in any implant containing metal. This particular corrosion was identified through hip replacement implants because of the immense number of hip replacement surgeries per year (~300,000/yr), and the reported patient pain in the surrounding tissue as the hip degrades. However, the increasing commonality of joint replacement surgeries, medical implants, and implantable biosensors combined with an increase in ambient electromagnetic activity of a technologically advanced society could result in significant unknown, adverse human health effects as metals corrode unexpectedly in the body.

Modern developments in biosensing have allowed for increased implementation of precision medicine practices. Precision medicine uses precise, directed action to treat and prevent patient morbidities with minimal medication and invasion beyond the target area, and is the underlying goal of many modern and future treatment methods. However, such targeted action requires significant knowledge and data for the particular morbidity and affected tissue. One of the most notable and common implementations of precision medicine, currently, is in the treatment of diabetes. Continuously monitoring glucose systems provide real time data of blood glucose levels for actionable response of insulin injection. Predictive algorithms can anticipate glucose level peaks and troughs for the individual user, decreasing the required amount of total medication used. These systems rely on an implanted biosensor that can simultaneously sense glucose level and transmit the data to a handheld receiver. The transmitter is typically a metal based electrode manufactured from similar biocompatible alloys, as those within joint replacements mentioned previously. These sensors are typically changed every 30-90 days because of a thickened cell encapsulation layer of fibroblasts, fibrocytes, and collagen cells formed by the body's immunologic responses around the sensing probe that hinders accuracy. The potential corrosion of these electrodes is not discussed because of the short implanted life and lack of mechanical wear on the sensor. However, the work of the present invention indicates that the presence of electrical activity generated by the sensor itself could result in significant electrode corrosion and dissolution of metal into the body during the implanted life. Continual replacement and increased use of biosensors could lead to increased concern of metal toxicity within patients. The active electrochemical corrosion presented here could be considered in the future design of implanted devices and sensors.

What is claimed is:

1. A device for reducing corrosion of a medical implant, comprising:
   a medical implant;
   a dampening circuit coupled to the medical implant and configured to detect the presence of any electrical potential oscillations in the medical implant and to generate a signal that will at least partially dampen the electrical potential oscillations in the medical implant.

2. The device of claim 1, further comprising a pair of probes coupled to the dampening circuit and the medical implant.

3. The device of claim 2, wherein the dampening circuit comprises an operational amplifier in a unity inverting configuration.

4. The device of claim 3, wherein the dampening circuit further comprises a bipolar junction transistor in a common phase splitting circuit.

5. The device of claim 2, wherein the dampening circuit comprises a microcontroller having an embedded analog to digital converter and an arbitrary waveform generator.

6. The device of claim 5, wherein the microcontroller is programmed to record an input signal received from the pair of probes.

7. The device of claim 6, wherein the microcontroller is programmed to convert the input signal to a digital signal, to generate a phase shifted signal that is 180 degrees out of phase with the input signal, and to output the phase shifted signal to the pair of probes.

8. The device of claim 7, further comprising a constant feedback loop coupled to the microcontroller and the microcontroller is programmed to alter the phase shifted signal based on a feedback signal provided by the constant feedback loop.

9. The device of claim 2, wherein the electrical potential oscillations have a frequency in the range of 60 hertz to 1 gigahertz.

10. The device of claim 9, wherein the frequency is in the range of 60 hertz to 1 kilohertz.

11. A method of protecting a medical implant against corrosion, comprising the step of coupling a dampening circuit to the medical implant, wherein the dampening circuit is configured to detect the presence of any electrical potential oscillations in the medical implant and to generate a signal that will at least partially dampen the electrical oscillations in the medical implant.

12. The method of claim 11, wherein the dampening circuit is coupled to the medical implant by a pair of probes.

13. The method of claim 12, wherein the dampening circuit comprises an operational amplifier in a unity inverting configuration.

14. The method of claim 13, wherein the dampening circuit further comprises a bipolar junction transistor in a common phase splitting circuit.

15. The method of claim 11, wherein the dampening circuit comprises a microcontroller having an embedded analog to digital converter and an arbitrary waveform generator.

* * * * *